United States Patent [19]

Huszczuk

[11] Patent Number: 4,723,435
[45] Date of Patent: Feb. 9, 1988

[54] MEANS OF CONTROLLED SIMULATION OF RESPIRATORY GAS EXCHANGE FOR ON-LINE CALIBRATION OF RESPIRATORY ANALYZERS

[75] Inventor: Andrew R. Huszczuk, Long Beach, Calif.

[73] Assignee: Research and Education Institute, Inc., Harbor-UCLA Medical Center, Torrance, Calif.

[21] Appl. No.: 853,343

[22] Filed: Apr. 17, 1986

Related U.S. Application Data

[60] Continuation-in-part of Ser. No. 842,924, Mar. 24, 1986, Pat. No. 4,680,956, which is a division of Ser. No. 552,615, Nov. 17, 1983, abandoned.

[51] Int. Cl.$^4$ .................... G01N 33/497; G01D 25/00
[52] U.S. Cl. ..................................... 73/1 G
[58] Field of Search .................. 73/1 G, 866.4, 865.9, 73/432.1; 128/716, 719

[56] References Cited

U.S. PATENT DOCUMENTS

| | | | |
|---|---|---|---|
| 4,448,058 | 5/1984 | Jaffe et al. | 73/1 G X |
| 4,537,058 | 8/1985 | Luper | 73/1 G |
| 4,680,956 | 7/1987 | Huszczuk | 73/1 G |

FOREIGN PATENT DOCUMENTS

| | | | |
|---|---|---|---|
| 1959244 | 6/1971 | Fed. Rep. of Germany | 128/716 |
| 2541691 | 3/1977 | Fed. Rep. of Germany | 128/719 |

OTHER PUBLICATIONS

"A Piston Pump for Respiration Simulation"; *J. Appl. Physiology*; 50(3); pp. 663–664; pub. 1981; U. Boutellier et al.

"A Flow and Volume Calibrator for Respiratory Measuring Equipment"; *Journal of Medical Engineering & Technology* (GB); vol. 3, No. 5, pp. 248–251; Sep., 1979; A. Shaw et al.

*Primary Examiner*—Tom Noland
*Attorney, Agent, or Firm*—Drucker & Sommers

[57] ABSTRACT

A method and apparatus for the controlled simulation of respiratory gas exchange as it takes place in mammals, for the primary purpose of calibrating and checking the performance of laboratory and clinical test equipment systems. The method and apparatus can reproduce any range of respiratory performance by pumping and mixing atmospheric air with a gas mixture of carbon dioxide and nitrogen. This invention provides an accurate, economical and rapid apparatus for on-line calibration of analytical respiratory test systems.

18 Claims, 1 Drawing Figure

MEANS OF CONTROLLED SIMULATION OF RESPIRATORY GAS EXCHANGE FOR ON-LINE CALIBRATION OF RESPIRATORY ANALYZERS

This is a continuation-in-part of U.S. Ser. No. 842,924 filed Mar. 24, 1986 now U.S. Pat. No. 4,680,956, which was a division of U.S. patent application Ser. No. 552,615, filed Nov. 17, 1983 and now abandoned.

BACKGROUND OF THE INVENTION

1. Scope of the Invention

The present invention relates to an apparatus which can simulate any respiratory function in mammals for the purpose of calibrating analytical systems. The simulation is accomplished by a piston pump which "inhales" surrounding atmospheric air, composed approximately of 21% (by volume) oxygen and 79% nitrogen, and mixing said atmospheric air in varying proportions, with a pre-mixed volume of carbon dioxide and nitrogen, then "exhaling" the pre-determined gas mixture to simulate a particular respiratory performance evaluated by the test system to be calibrated.

Respiratory function can theoretically range from zero oxygen conversion (all oxygen inhaled is exhaled) to nearly total oxygen conversion (no free oxygen is exhaled). An approximation of total oxygen conversion can be found in nature in diving whales that can hold their breaths for as long as 45 minutes, during which time most of the oxygen is consumed. The exhaled gases of these diving whales approximate a mixture of about 17% carbon dioxide, by volume, in nitrogen.

The present invention utilizes a mixture of gases which in composition approximates a gas that a diving whale would exhale after total oxygen depletion. By diluting the gas mixture with a pre-determined amount of atmospheric air, any range of respiratory function can be simulated in a known mixture of "exhaled" $O_2$ - $CO_2$ - $N_2$ gas. By comparing the known parameters of the respiratory simulator with the results given by the analytical respiratory equipment being calibrated, the accuracy of such analytical equipment can be verified.

2. Prior Art

Prior to the use of respiratory simulators, in order to calibrate an analytical respiratory equipment system, a biological subject would have its expired gases collected at the outlet of said system and subjected to tedious classical analyses and manual calculations. The variables of respiration of this subject monitored by the laboratory or clinical test system and results of said analysis would be compared. This type of calibration was crude at best since the biological subject could not produce uniform, controlled, respiration and metabolic rate.

A respiratory simulator has also been previously developed, by others, to simulate inspiration and expiration using a double piston pump (*A Piston Pump for Respiration Simulation;* U. Boutellier, U. Gomez, and G. Mader; J. Appl. Physiology, 50(3): 663–664, 1981). The Boutellier et al double piston simulator utilizes one cylinder as the inspiratory chamber, "inhaling" atmospheric air, while the other cylinder acted as the expiratory chamber, "exhaling" a pre-mixed $O_2$ - $CO_2$ - $N_2$ gas mixture. While this system provides on-line analysis of known volumes and compositions of gases, it requires the use of an expensive pre-mixed gas for the calibration. Because the pre-mixed gas mixture was solely used as the expiratory gas, only one composition of expired gas could be used for calibration purposes. To vary compositions, different tanks of pre-mixed $O_2$-$CO_2$-$N_2$ gases of exact known compositions would be required, and this approach to on-line calibration thus becomes very expensive.

In general, the invention relates to a respiratory simulator that replaces biological subjects to test the accuracy and calibrate the performance of respiratory analysis equipment. The simulation of respiration is accomplished by a single cylinder piston pump that inhales atmospheric air and mixes it with a calibration gas composed of $CO_2$ and $N_2$. The pump then "exhales" the mixture of gases at known concentrations and known frequencies and volumes and compares the results given by the analytical equipment. The present invention thus allows simplified on-line automatic calibration of respiratory and metabolic analysis equipment over a wide range of exhalation products.

SUMMARY OF THE INVENTION

The present invention simplifies the Boutellier et al. apparatus by providing a single chambered piston pump. Furthermore, only one tank of a calibrating gas mixture is required, the calibrating gas mixture initially containing no oxygen and about 17% $CO_2$ in $N_2$, by volume. Such zero oxygen calibrating mixture simulates maximum oxygen utilization or maximum oxygen efficiency on the respiration cycle. The calibrating mixture parameters are readily varied to simulate any other (desired) levels of gas exchange by introducing a given volume of air into the individual calibrating gas mixture.

Also, the volume of the calibrating $CO_2$ - $N_2$ gas mixture initially required is reduced by about 75% since the mixture is diluted by cost-free atmospheric air. Indeed, the cost of purchasing the initial $CO_2$ - $N_2$ gas mixture can be further reduced by introducing the $CO_2$ and $N_2$ into the simulator from separate tanks and mixing just prior to entering the respiratory apparatus. The present invention thus reduces calibration time from hours to minutes, and greatly reduces the cost of expensive pre-mixed gases.

DETAILED DESCRIPTION OF THE INVENTION

Figure 1:
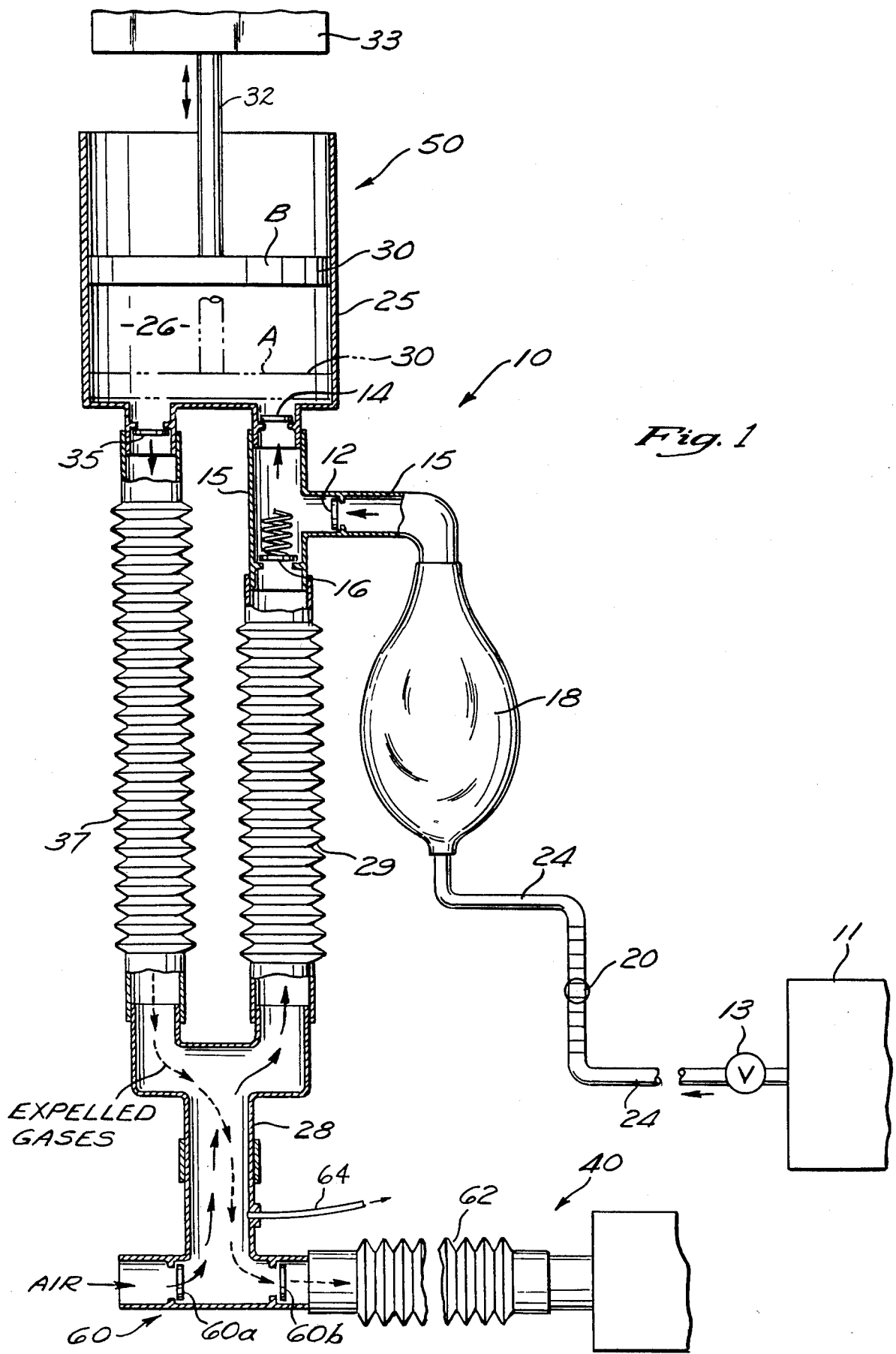

The respiratory simulation apparatus of this invention is shown schematically in FIG. 1 and is designated generally by the numeral 10. The apparatus comprises a calibration gas source, e.g. tank 11 which contains preferably a pre-mixed, commercially available source of carbon dioxide ($CO_2$) in nitrogen. Typically, a 17% mixture of $CO_2$ in $N_2$, by volume, is introduced into tank 11. However, a range of mixtures of 15–20% $CO_2$ in $N_2$, by volume, can be initially introduced into tank 11 as the calibration gas.

The pre-mixed calibration gases are fed, via calibration tank outlet valve 13, to inlet conduit pipe 24, and thence to a flexibly-walled collapsible bag or bladder 18, via a rotameter 20. In this manner, the calibration gas is introduced to the bladder 18 at a controlled and monitored flowrate and known composition. Alternatively, separate $CO_2$ and $N_2$ tanks can feed these gases to the bladder 18 through conventional rotameter devices to achieve a pre-mixed gas in the bladder. The bladder 18 serves as a temporary storage medium for the calibration gas, the gas residing temporarily in bladder 18 at atmospheric pressure.

The calibration gas is drawn into a piston chamber 26 as follows. The upward stroke of the piston 30 in piston chamber 26 (powered by reciprocating device 33), simulates the inhalation phase of respiration and the downward piston stroke simulates the exhalation phase of respiration. During the upward stroke of the piston 30 within piston cylinder 25 from position A to position B, the pressure in chamber 26 is reduced and the calibration gas is sucked into the piston chamber 26 through conventional one-way pressure valves 12 and 14 automatically opening under any pressure differential set up between bladder 18 and chamber 26 during the upward stroke of piston 30. Thus, the $CO_2$ - $N_2$ calibration gas commences to enter the single piston chamber 26 of piston cylinder 25 as the upward stroke of piston 30 commences.

As soon as the bladder 18 is essentially evacuated, e.g. to 5-10 cm of water below atmospheric pressure, spring-loaded valve 16 in conduit 15 is pre-set to open, thereby allowing atmospheric air to enter piston chamber 26 via inspiratory port 60a of a conventional two-way breathing valve 60 usually constituting the inital stage of the analyzer 40 being tested. Breathing valve 60 is usually affixed to mouthpiece or facemask interface 28 of the respiratory apparatus of this invention. The air then passes through corrugated tube or means 29, valves 16 and 14, and mixes with the previously introduced, known quantity of $CO_2$ and $N_2$ in piston chamber 26.

The volume of gas entering piston chamber 26 (which is equivalent to the inhalation phase of the respiratory cycle) is controlled by the extent of stroke displacement of the piston 30 within piston cylinder 25. Thus, the piston 30 is provided with a piston rod 32, connected for reciprocal movement to a conventional reciprocating device 33. The reciprocating device 33 controls the stroke displacement of the piston rod 32 and thereby the volume of the chamber 26 within piston cylinder 25. The stroke displacement of piston rod 32 is made variable by conventional means, as is the frequency of reciprocation of the piston rod 32 and its associated piston 30.

The upward stroke displacement of piston 30 is followed by a downward stroke displacement of piston 30 under the influence of reciprocal power means 33. The downward stroke simulates the exhalation phase of the respiratory cycle, and during the exhalation phase, the mixture of $O_2$, $CO_2$ and $N_2$ are expelled through one-way outlet valve means 35, through a corrugated conduit pipe or means 37, to a tested respiratory metabolic analysis system 40, shown schematically in FIG. 1.

During the downward stroke of piston 30, calibration gas continues to flow, via line 24, under a controlled and monitored flowrate to bladder 18 so that, during the exhalation phase of the piston cycle, the bladder 18 is again filled with a known volume or amount of calibration gas. And upon commencement of the upward (rearward) stroke of the piston 30, the calibration gas will be "sucked in" to the chamber 26, to repeat the respiratory cycle, as previously described.

The rate of bleeding of calibration gas to the bladder 18, the extent of stroke displacement, and frequency of displacement of piston 30 are all readily altered to simulate a variety of metabolic and respiratory states of a biological subject.

OPERATION OF THE SIMULATED RESPIRATION APPARATUS

During the phase of the pump cycle simulating inhalation, piston 30 is upwardly drawn (as shown in FIG. 1) from dotted line position A to solid line position B in piston cylinder 25, providing reduced pressure and increased volume within piston chamber 26. The reduction in pressure causes inspiratory pressure-responsive valve 14 and pressure-responsive bladder valve 12 to open, allowing the calibration gas to be substantially evacuated from bladder 18, e.g. down to 5-10 cm. of water, below atmospheric pressure. Spring-loaded valve 16 is preset to open only after bladder 18 is essentially collapsed. As spring-loaded valve 16 opens, atmospheric air passes therethrough, through conduit 15 and through valve 14 to mix with the calibration gas within piston chamber 26. The amount of air volume introduced into chamber 26 is determined by the stroke displacement of piston 30 in the upward (inhalation) phase of the piston cycle minus the amount of gas previously drawn from the bladder 18 (the calibration gas representing the simulated metabolic rate taking place in a biological subject). Typically, about 250-300 cc of calibration gas and about 700-750 cc of air are introduced into chamber 26 during the inhalation phase of the respiratory cycle.

During the downward phase of the pump cycle simulating exhalation, the reciprocating device 33 forces piston 30 towards the valved lower end of piston cylinder 25 to dotted line position A, and inspiratory valve 12 and spring-loaded valve 16 close. The decreasing volume of piston chamber 26 increases the pressure on the gases within until one-way pressure-responsive expiratory valve 35 opens. The forward motion of piston 30 evacuates the gases from piston chamber 26 so that the gases are released, via a corrugated conduit means 37, through mouthpiece interface 28, one-way pressure valve 60b, corrugated conduit 62 and thence into the subsequent stages of respiratory analysis system and equipment 40 being tested. A portion of the released gases may exit mouthpiece 28 by line 64.

As the piston 30 reaches the maximum position of exhalation (position A in FIG. 1), the cycle of the reciprocating device 33 reverses, thereby restarting the inhalation cycle as aforedescribed.

This cycle of inspiration and expiration of gases occurs repetitively and reproducibly. The volume displacement of the piston chamber 26 determines the simulated tidal volume (the volume of a single breath) and the rate of repitition of the cycling of the piston multiplied by the tidal volume will determine the minute ventilation of the lungs.

The volume of inlet and outlet gas mixture is controlled by the power means to piston rod 32. Since the calibration gas composition, as well as its flow rate, the atmospheric air composition, the tidal volume and the cycling rate are all known, all parameters that are calculated by the analytical system can be directly compared. These parameters include breath-by-breath value determinations of tidal volume ($V_T$), ventilatory minute volume ($V_E$), respiratory frequency, (f), respiratory gas exchange ratio (R), $O_2$ consumption ($VO_2$) and $CO_2$ production ($VCO_2$). These parameters reflect directly on the fitness of biological subjects to be studied on the respiratory analysis devices.

Features of this invention combine calibration and evaluation procedures. Any quantity of respiratory or gas exchange variables can be chosen, executed at will and "on line" confronted with readings produced by respiratory processing equipment or setup, so that the readjustment and tuneup procedures can be performed quickly and precisely. As a result, the entire calibration procedure takes minutes instead of hours. The method and means of this invention also utilizes only about 25% of an otherwise required quantity of expensive calibrating gas mixtures, as compared with Boutellier et al, and effects a very substantial saving in manpower and cost over manual methods of calibration.

The rotameter and one-way valves utilized in the calibration system of this invention are inexpensive, simple and reliable. Further, the valving means between the bladder 18 and conduit means 29 may be further simplified as by elimination of the spring loaded valve 16, and replacing it with a simple orifice, in which case there will be a simultaneous air and calibration gas inflow to piston chamber 26 during the upward stroke of piston 30. Rotameter 20 and valve 13 controlling flow from calibration gas cylinder 11 may be replaced with gas dispenser devices of many other types.

The aforesaid 15-20% $CO_2$ in $N_2$, as a calibration mixture, corresponds to the expiratory exchange ratio R (volume $CO_2/O_2$) ranging from 0.714 to 0.952, respectively, which covers approximately 99% of the real life physiological range. There is, however, a good possibility that an expiratory exchange ratio of R=1 would be more expeditiously utilized some existing respiratory analysis systems, namely, those systems which measure only the expired volume of gases and do not measure the inspired volume of gases. The apparatus of this invention will simulate R=1 with a 21% $CO_2$ in $N_2$ calibrating mixture. It is, therefore, of advantage to employ R=1, in these systems.

The theoretical basis that gives advantage of R=1 over any other R value is that, only with R=1, are the inspired and expired volumes of gases exactly equal in physiological situations, and therefore the analyzer systems which measure only the expired volume do not require in this case any correctional computations. A. B. Otis describes the error relationship between the R valve and the inspired volume of oxygen in chapter 27 of Handbook of Physiology, Respiration, pp. 681-685, Washington, D.C. 1964. His equation 17 on page 684 determines the percentage error as follows:

$$\% \text{ Error} = FIO_2 (1-R) \times 100$$

where $FIO_2$ denotes the fractional concentration of inspired oxygen (0.21 for air breathing). Thus, for R=1, the whole expression becomes zero and the % error is also zero. When the $CO_2$ in $N_2$ in the calibration mixture is 20%, the % error is:

$$\% \text{ Error} = 0.21 (1-20/21) \times 100 = 0.21 \times 0.048 \times 100 = 1\%$$

Thus, employing a substantially 21% $CO_2$ in $N_2$ range of calibration mixtures, increases the usefulness and accuracy of the calibration equipment of this invention with those analyzer systems which measure only expired gas volumes. In those systems in which inspired gas volume is also measured, a 15-21% $CO_2$ in $N_2$ calibration mixture is employed and the correctional factor taken into account. In all instances, however, a substantially 21% $CO_2$ in $N_2$ calibration mixture will ensure the most accurate calibration.

Further modifications of the method and means of this invention will be obvious to those skilled in the art.

I claim:

1. A method for simulating the respiratory cycle of a biological subject, in a respiratory analysis system which comprises the steps of:
   (a) in a first phase of said respiratory cycle
      (1) introducing a known volume of oxygen-free carbon dioxide in nitrogen gases to a single piston chamber from a first source; and
      (2) introducing a known volume of air to said chamber from a second source for admixture with said carbon dioxide in nitrogen in said single piston chamber, said gases, introduced into said single piston chamber, from both said first source and said second source, simulating inhalation, and a given metabolic rate;
   (b) in a second phase of said respiratory cycle
      (1) expelling said admixed air, carbon dioxide and nitrogen gases from said single piston chamber, said expelling of said gases simulating exhalation and a pre-determined metabolic rate;
   (c) repeating said first and second phases of said respiratory cycle in a uniform manner; and
   (d) introducing said expelled gases into said respiratory analysis system for calibration and adjustment of said respiratory analysis system with reference to the known compositions and volumes of gas expelled from said single piston chamber.

2. The method of claim 1 wherein said second source is the atmosphere.

3. The method of claim 1 wherein the volume of carbon dioxide and nitrogen gases introduced to said chamber during the respiratory phase of each cycle, is varied to simulate differing metabolic rates.

4. The method of claim 1 wherein the carbon dioxide in nitrogen gases entering said chamber ranges from between about 15-21%, by volume, of carbon dioxide in nitrogen.

5. The method of claim 1 wherein air is introduced into said chamber after said carbon dioxide in nitrogen has been introduced into said chamber.

6. The method of claim 1 wherein the known volume of said carbon dioxide in nitrogen gases from said first source comprises about 15-21% by volume of carbon dioxide in nitrogen and are introduced into said chamber and said air, from said second source is automatically introduced into said chamber after introduction of said known volume of carbon dioxide in nitrogen has been completed.

7. The method of claim 1 wherein the frequency of the respiratory cycle is varied.

8. The method of claim 1 wherein the air is introduced into said chamber simultaneously with said carbon dioxide and nitrogen gases.

9. The method of claim 1 wherein the carbon dioxide in nitrogen gases entering said chamber ranges from between substantially 21%, by volume, of carbon dioxide in nitrogen.

10. A method of on-line calibration of a respiratory analysis system for a biological subject which comprises:
   (a) introducing a known volume of oxygen-free carbon dioxide in nitrogen to a single piston chamber from a first source;
   (b) introducing a known volume of air to said chamber from a second source for admixture with said carbon dioxide in nitrogen in said single piston chamber, said gases, introduced into said single piston chamber from said first source and said second source, simulating inhalation, and a given metabolic rate, in said subject;

(c) expelling said admixed air, carbon dioxide and nitrogen from said single piston chamber, said expelling of said gases simulating exhalation and a predetermined metabolic rate in said subject;

(d) introducing said expelled gases into said respiratory analysis system, for calibration of said analysis system with reference to the known compositions and volumes of gases expelled from said chamber; and said steps (a), (b), (c), and (d) comprising a respiratory cycle and repeating said respiratory cycle in a reproducible manner for a pre-determined number of cycles.

11. The method of claim 10 wherein said second source is the atmosphere.

12. The method of claim 10 wherein the combined volume of carbon dioxide and nitrogen gases introduced to said chamber is varied to simulate differing metabolic rates.

13. The method of claim 10 wherein the carbon dioxide in nitrogen gases entering said chamber ranges from between about 15–21%, by volume, of carbon dioxide in nitrogen to simulate differing respiratory exchange ratios.

14. The method of claim 10 wherein air is introduced into said chamber after said carbon dioxide in nitrogen has been introduced into said chamber.

15. The method of claim 10 wherein the frequency of the respiratory cycle is varied.

16. The method of claim 10 wherein the air is introduced into said chamber simultaneously with said carbon dioxide and nitrogen gases.

17. The method of claim 10 wherein the known volume of said carbon dioxide in nitrogen gases from said first source comprises about 15–21% by volume of carbon dioxide in nitrogen and are introduced into said chamber and said air, from said second source is automatically introduced into said chamber after introduction of said known volume of carbon dioxide in nitrogen has been completed.

18. The method of claim 10 wherein the carbon dioxide in nitrogen gases entering said chamber ranges from substantially 21% by volume, of carbon dioxide in nitrogen to simulate differing respiratory exchange ratios.

* * * * *